United States Patent [19]
Yeske et al.

[11] Patent Number: 5,561,214
[45] Date of Patent: Oct. 1, 1996

[54] HYPERBRANCHED POLYASPARTATE ESTERS AND A PROCESS FOR THEIR PREPARATION

[75] Inventors: Philip E. Yeske; Lyuba K. Gindin, both of Pittsburgh; Douglas A. Wicks, Mt. Lebanon; E. Haakan Jonsson, Coraopolis, all of Pa.

[73] Assignee: Bayer Corporation, Pittsburgh, Pa.

[21] Appl. No.: 443,505

[22] Filed: May 18, 1995

[51] Int. Cl.$^6$ .......................... C08G 69/48; C07C 229/24
[52] U.S. Cl. .......................... 528/363; 525/418; 525/419; 525/420; 528/328; 528/332; 528/335; 528/345; 560/170; 560/171
[58] Field of Search .................................. 525/418, 419, 525/420; 528/328, 332, 335, 345, 363; 560/170, 171

[56] References Cited

U.S. PATENT DOCUMENTS 5,126,170  6/1992  Zwiener et al. .................... 427/385.5

FOREIGN PATENT DOCUMENTS 2158945  5/1973  Germany .
93/21259  10/1993  WIPO .

OTHER PUBLICATIONS

"The solid-phase synthesis of dendrtitic polyamides", Uhrich et al, Polymer Bulletin 25, pp. 551 to 558 (Month unavailable) 1991.

"Synthesis, Characterization, and Curing of Hyperbranched Allyl Ether–Maleate Functional Ester Resins", by Johansson et al, Journal of Polymer Science: Part A: Polymer Chemistry, vol. 31, pp. 617–624 (Month unavailable) 1993.

"High–Solid Alkyds Based on Hyperbranched (Dendritic) Polymers—A New Concept with New Opportunities", by Pettersson et al, presented at the Waterborne, Higher–Solids and Powder Coatings Symposium, Feb. 9–11, 1994.

"Chemistry of Dendritic Molecules Holds Growing Allure for Researchers", Chemical Engineering News, Feb. 1, 1993.

"Dendrimers Nearing Availability for Commercial Evaluation," Chemical & Engineering News, Aug. 16, 1993.

Primary Examiner—Shelley A. Dodson
Attorney, Agent, or Firm—Joseph C. Gil; Thomas W. Roy

[57] ABSTRACT

The present invention relates to hyperbranched polyaspartate esters containing repeating structural units corresponding to the formula I and/or II

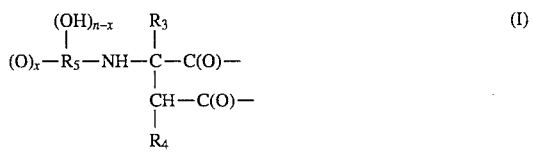

The present invention also relates to a process for the preparation of these hyperbranched polyaspartate esters by self condensing, via a transesterification reaction, at least a portion of the hydroxy and ester groups of the hydroxy aspartates corresponding to the above formula at a temperature of 60° to 240° C. to form hyperbranched polyaspartate esters and eliminating alcohols having the formula $R_1$—OH and/or $R_2$—OH.

9 Claims, 1 Drawing Sheet

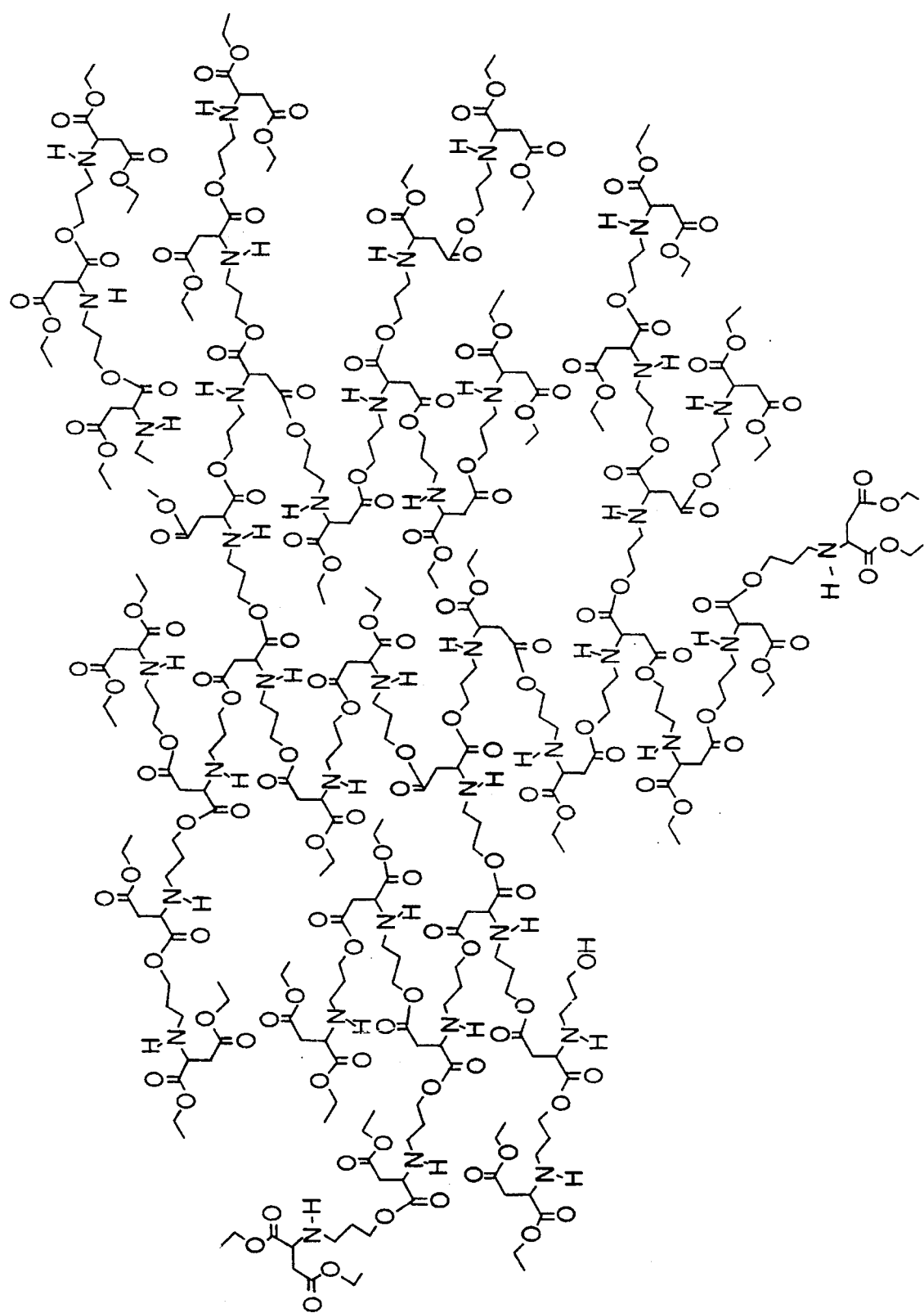

HYPERBRANCHED POLYASPARTATE ESTERS AND A PROCESS FOR THEIR PREPARATION

BACKGROUND OF THE INVENTION

1. Field of the Invention

This present invention relates to hyperbranched amine-functional polyesters, i.e., polyaspartate esters, and to a method for their preparation by the self condensation of hydroxy aspartate esters via a transesterification reaction.

2. Description of the Prior Art

Coating compositions containing, as binders, polyisocyanates in combination with polyaspartates containing secondary amino groups are known and disclosed in U.S. Pat. No. 5,126,170 and also DE-OS 2,158,945. However, the functionality of these polyaspartates is limited to the functionality of the starting polyamine. Higher functionalities are required to provide increased hardness as well as solvent resistance. However, as the functionality of these polyaspartates increases, the viscosity also increases such that more solvent is required to reduce the viscosity of the composition to typical application levels.

It is an object of the present invention to provide highly functional resins, which have a low viscosity and may be used for various applications, especially for the production of coatings having a high degree of hardness and solvent resistance.

This object may be achieved with the hyperbranched amine-functional polyesters according to the present invention that are described in more detail below. It is surprising that these amine-functional polyesters can be prepared since it would be expected that they would not be stable enough to satisfy this object due to the well known fact that amines cause the degradation of ester groups.

Hyperbranched polymers have been disclosed in the prior art. See, for example, PCT application WO 93/21259, "The Solid-Phase Synthesis of Dendritic Polyamides" by Uhrich et al, Polymer Bulletin 25, pg. 551 to 558 (1991); "Synthesis, characterization, And Curing of Hyperbranched Allyl Ether-Maleate Functional Ester Resins" by Johansson et al, J. of Polymer Science: Part A: Polymer Chemistry, Vol. 31, pg. 619–624 (1993); "High-Solid Alkyds Based on Hyperbranched (Dendritic) Polymers—A New Concept with New Opportunities" by Pettersson et al, presented at the Waterborne, Higher-Solids, and Powder Coatings Symposium, Feb. 9–11, 1994; "Chemistry of Dendritic Molecules Holds Growing Allure for Researchers," Chemical & Engineering News, Feb. 1, 1993; and "Dendrimers Nearing Availability for Commercial Evaluation," Chemical & Engineering News, Aug. 16, 1993.

None of the preceding references teach or suggest the amine-functional polyesters according to the present invention.

SUMMARY OF THE INVENTION

The present invention relates to hyperbranched polyaspartate esters containing repeating structural units corresponding to formula I

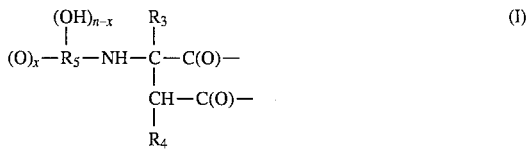

wherein $R_3$ and $R_4$ may be identical or different and represent hydrogen or organic groups which are inert towards isocyanate groups at a temperature of 100° C. or less, and $R_5$ represents a hydrocarbon radical containing at least two carbons, n has a value of 1 to 3 and x has a value of 1 to 3, but cannot be greater than n.

The present invention also relates to a process for the preparation of hyperbranched polyaspartate esters by self condensing, via a transesterification reaction, at least a portion of the hydroxy and ester groups of hydroxy aspartates corresponding to the formula

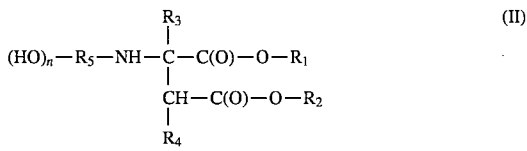

wherein $R_1$ and $R_2$ may be identical or different and represent organic groups which are inert towards isocyanate groups at a temperature of 100° C. or less, and $R_3$, $R_4$, $R_5$ and n are as defined above, at a temperature of 60° to 240° C. to form hyperbranched polyaspartate esters and eliminating alcohols having the formula $R_1$—OH and/or $R_2$—OH.

BRIEF DESCRIPTION OF THE DRAWING

The FIGURE sets forth an example of a hyperbranched polyaspartate ester which may be obtained according to the present invention.

DETAILED DESCRIPTION OF THE INVENTION

Suitable hydroxy aspartates for use as starting materials according to the invention are prepared by reacting optionally substituted maleic or fumaric acid esters with amino alcohols. Suitable optionally substituted maleic or fumaric acid esters are those corresponding to the formula $$R_1OOC-CR_3=CR_4-COOR_2$$

wherein $R_1$ and $R_2$ may be identical or different and represent organic groups which are inert towards isocyanate groups at a temperature of 100° C. or less, preferably an alkyl radical containing 1 to 9 carbon atoms, more preferably methyl, ethyl or butyl groups and $R_3$ and $R_4$ may be identical or different and represent hydrogen or organic groups which are inert towards isocyanate groups at a temperature of 100° C. or less, preferably hydrogen.

Examples of optionally substituted maleic or fumaric acid esters suitable for use in the preparation of the compounds corresponding to formula I include dimethyl, diethyl and dibutyl (e.g., di-n-butyl) esters of maleic acid and fumaric acid and the corresponding maleic or fumaric acid esters substituted by methyl in the 2- or 2- and 3-position.

Suitable amino alcohols for preparing the hydroxy aspartates are those containing one primary amino group and at least one, preferably 1 to 3, and more preferably 1 hydroxy group, provided that the hydroxy group(s) are aliphatically (including araliphatically) or cycloaliphatically bound. These amino alcohols correspond to the formula $$H_2N-R_5-(OH)_n$$

wherein $R_5$ represents the hydrocarbon radical obtained by removing the amino and hydroxyl groups from an amino alcohol and n has a value of 1 to 3, preferably 1.

Suitable amino alcohols include ethanolamine, 1-amino-2-hydroxypropane, 1-amino-3-hydroxypropane, 1-hydroxy-2-aminopropane and 1,3-propanolamine, the isomeric butanol amines, 2-amino-1,3-propane diol, 2-amino-2-hydroxymethyl-propane diol and 4-hydroxymethyl aniline. The monohydroxy amines are preferred, especially ethanolamine and the isomeric propanol and butanol amines.

The preparation of hydroxy aspartates takes place by the Michael addition of the amino alcohol to the unsaturated diester at a temperature of 0° to 100° C. using the starting materials in such proportions that at least 1, preferably 1, olefinic double bond is present for each primary amino group. Excess starting materials may be removed by distillation after the reaction. The reaction may be carried out solvent-free or in the presence of suitable solvents such as methanol, ethanol, propanol, dioxane, tetrahydrofuran, pyridine, dimethyl formamide, nitromethane and mixtures of such solvents.

The hyperbranched polyaspartate esters according to the invention are prepared by the self condensation of the hydroxy aspartates via a transesterification reaction at an elevated temperature of 60° to 240° C., preferably 70° to 200° C. and more preferably 80° to 140° C., optionally in the presence of a known transesterification catalyst. Examples of suitable catalysts include the known titanium, tin, zinc, antimony and lead compounds, such as titanium(IV) butoxide, tetrakis(2-ethylhexyl)-titanate, tin(IV) oxide, dibutyltin oxide, dioctyltin oxide, dibutyltin dilaurate, dioctyltin dilaurate, butyltin hydroxide oxide, octyltin hydroxide, zinc(IV) oxide, zinc(II) oxide, lead phenolate and lead acetate.

The invention may be illustrated by the following reaction scheme using an aspartic acid ester containing one secondary amino group and one hydroxy group as the starting material. Two hydroxy aspartate molecules react to form a polymer corresponding to formula III or formula IV:

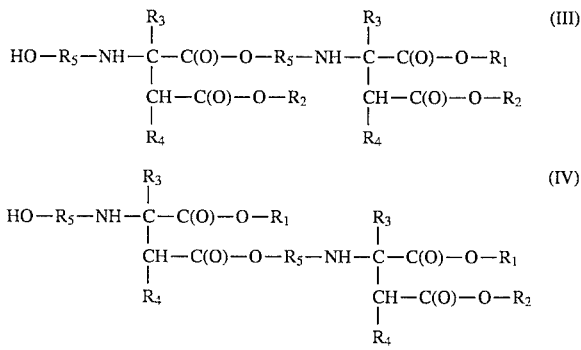

The compound represented by formula III is formed by the transesterification of the $R_1$ group, while the compound represented by formula IV is formed by the transesterification of the $R_2$ group. The next hydroxy aspartate molecule may be incorporated by transesterification of any of the remaining $R_1$ or $R_2$ groups. Because both of the $R_1$ and $R_2$ groups on any particular hydroxy aspartate molecule may be transesterified, substantial branching is present in the resulting product. Thus, these products as referred to as being hyperbranched.

The FIGURE sets forth an example of a hyperbranched amine-functional polyester which may be obtained according to the invention. The exact structure cannot be determined because it is not possible to predict if both of the ester groups will be transesterified. However, hypothetical structures can be set forth on the basis of a random transesterification reaction. The structure set forth in the FIGURE was obtained by the self polymerization of the hydroxy aspartate prepared from diethyl maleate and 3-aminopropanol and contains 39 secondary amino groups, 39 terminal esters and 1 hydroxy group.

The reaction is continued until the desired degree of polymerization is obtained. For each mole of starting material that takes part in the polymerization reaction, an additional amino group is incorporated into the polymer. The course of the reaction may be monitored from the evolution of monoalcohols corresponding to the formulas $R_1$—OH and/or $R_2$—OH.

In another embodiment of the present invention the hydroxy aspartates may be blended with non-amine containing hydroxy acids or the corresponding esters as comonomers for the self condensation reaction. The resulting products will have a similar structure to formula IV) above with the exception that the number of amino groups will be reduced. These non-amine containing hydroxy acids may be present in an amount of 0 to 80% by weight, based on the total weight of the monomers. Examples of suitable hydroxy acids or esters include methyl-2-hydroxybutyric acid, 1,6-hydroxyhexadecanoic acid, glycolic acid, 2-hydroxyisobutyric acid, (+/−)-2-hydroxy-3-methylbutyric acid, (+/−)-2-hydroxycaproic acid, 1,2-hydroxystearic acid, lactic acid, (+/−)-3-hydroxybutyric acid, 10-hydroxydecanoic acid, 2,2-bis-hydroxymethyl propionic acid, 2-hydroxy-2-methylbutyric acid, (+/−)-2-hydroxyisocaproic acid, 1,2-hydroxy-dodecanoic acid, DL-malic acid, citric acid, 3-hydroxy-3-methylglutaric acid, and the corresponding esters.

The resulting hydroxy polyaspartates have a number average molecular weight ($M_n$) of 400 to 200,000, preferably 1000 to 80,000, and an average amino group functionality of 2 to 500, preferably 5 to 200. These products are distinguished by a very high secondary amine content, a low viscosity (compared to the viscosity of other polymers having a comparable functionality) and a surprising selectivity for the formation of ester groups without any detectable amide formation.

In an optional embodiment according to the invention, the terminal hydroxy group of the hyperbranched polyaspartate esters may be capped for example, with mono-, di- or polyfunctional carboxylic acids or their esters, such that the products only contain secondary amino groups. Preferably, monofunctional or difunctional, more preferably monofunctional, carboxylic acids and esters, more preferably esters, are used for this purpose.

The hyperbranched polyaspartate esters according to the invention are suitable for various applications such as binder components for the production of various polyureas for use as coatings, adhesives, foams, elastomers, microcellular elastomers, and also as ion exchange resins, biologically active systems, rheology modifiers, imaging materials, pigment dispersants, acid scavengers, corrosion inhibitors, emulsifiers/transport agents and as building blocks for additional materials, e.g., polyamides.

In a preferred embodiment the hyperbranched polyaspartate esters are reacted with polyisocyanates to form polyureas, which according to the present invention are understood to mean polymers containing urea groups and optionally other groups such as urethane groups.

Examples of suitable polyisocyanates include polyisocyanate monomers such as 4-isocyanatomethyl-1,8-octamethylene diisocyanate and polyisocyanate adducts, i.e., polyisocyanates containing isocyanurate, uretdione, biuret, urethane, allophanate, carbodiimide and/or oxadiazinetrione groups. The polyisocyanates adducts generally have an average functionality of 2 to 6 and an NCO content of 5 to 30% by weight. Preferred polyisocyanate adducts are the polyisocyanates containing isocyanurate groups, biuret groups or mixtures of isocyanurate groups with either allophanate and/or uretdione groups.

The polyisocyanate adducts are prepared from organic diisocyanates in known manner. Preferred organic diisocyanates include 1,6-hexamethylene diisocyanate, 1-isocyanato-3-isocyanatomethyl-3,5,5-trimethylcyclohexane (isophorone diisocyanate or IPDI), bis-(4-isocyanatocyclohexyl)-methane, $\alpha,\alpha,\alpha',\alpha'$-tetramethyl-1,3- and/or -1,4-xylylene diisocyanate, 1-isocyanato-1-methyl-4(3)-isocyanatomethyl cyclohexane, 2,4- and/or 2,6-toluylene diisocyanate, and 2,4- and/or 4,4'-diphenylmethane diisocyanate. Especially preferred diisocyanates are 1,6-hexamethylene diisocyanate and isophorone diisocyanate.

The hyperbranched polyasparatate esters and polyisocyanates are used in amounts sufficient to provide an equivalent ratio of isocyanate-reactive groups to isocyanate groups of about 0.5:1 to 20:1, preferably about 0.8:1 to 2.1 and more preferably about 0.8:1 to 1.5:1.

Preparation of the binders is carried out solvent-free or in the presence of the solvents conventionally used in polyurethane or polyurea coatings. It is an advantage of the process according to the invention that the quantity of solvent used may be greatly reduced when compared with that required in conventional two-component systems containing polyisocyanates and organic polyols having comparable functionalities to the hyperbranched polyasparatate esters according to the invention.

Examples of suitable solvents include xylene, butyl acetate, methyl isobutyl ketone, methoxypropyl acetate, N-methyl pyrrolidone, Solvesso solvent, petroleum hydrocarbons, isobutanol, butyl glycol, chlorobenzenes and mixtures of such solvents.

In the coating compositions according to the invention, the ratio by weight of the total quantity of binder components a) and b) to the quantity of solvent is about 40:60 to 100:0, preferably about 60:40 to 100:0.

The coating compositions may also contain other auxiliary agents and additives conventionally used in polyurethane and polyurea coatings, in particular, catalysts, pigments, fillers, levelling agents, antisettling agents, UV stabilizers and the like.

To prepare coatings, the coating compositions according to the invention are applied as one or more layers to substrates by known methods such as spraying, brush coating, immersion or flooding or by means of rollers or doctor applicators. The coating compositions according to the invention are suitable for the formation of coatings on various substrates, e.g., metals, plastics, wood, cement, concrete or glass. The coating compositions are particularly suitable for the formation of coatings on sheet steel, for example, for the manufacture of car bodies, machine trim panels, vats or containers. The substrates to be coated by the process according to the invention may be treated with suitable primers before the process according to the invention is carried out.

After the substrates exemplified above have been coated, the coatings may be cured at either ambient temperature, e.g., by air drying or so-called forced drying, or at elevated temperature. It is of great benefit that the resins will not thermally degrade even if they are cured at or exposed to higher than desired temperatures, e.g., which may occur in the event of a breakdown in an application line of a plant.

The invention is further illustrated but is not intended to be limited by the following examples in which all parts and percentages are by weight unless otherwise specified.

EXAMPLES

The following starting materials were used in the examples:

Preparation of hydroxy aspartate ester 172.0 parts of diethyl maleate (DEM) was charged into a flask under nitrogen and then 75.0 parts of 3-amino propanol (PA) was added dropwise to the maleate while the temperature was maintained at 60° C. The reaction was completed over a time period of 7 hours.

Preparation of hydroxy polyaspartate ester

The hydroxy aspartate ester described above was heated to 120° C. under vacuum in the presence of 0.03% by weight of titanium(IV) butoxide as the transesterification catalyst. Almost immediately the evolution of ethanol as a distillate started and was collected in a dry ice vacuum trap. The evolution of ethanol is indicative of the self condensation of the hydroxy aspartate ester starting material via the transesterification reaction set forth above in formula III. The reaction was continued until the desired estimated degree of polymerization was attained as indicated by recovered ethanol. The following table sets forth the reaction conditions and properties of the resulting product for two hyperbranched polyaspartate esters according to the invention.

|  | Example 1 | Example 2 |
|---|---|---|
| Monomer Charge | 100 | 250 |
| Reaction Time | 7 hr. | 13 hr. 30 min. |
| Ethanol Recovered (% of maximum from complete reaction) | 90.7 | 99 |
| Theoretical $M_n$ | 2246 | 9277 |
| OH Number ($M_n$) | 41 (1368) | 6 (9350) |
| Amine Number | 254 | 246 |
| Viscosity | 5200 | 25000 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A hyperbranched polyaspartate ester containing repeating structural units corresponding to the formula I

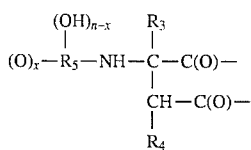 (I)

wherein $R_3$ and $R_4$ may be identical or different and represent hydrogen or organic groups which are inert towards isocyanate groups at a temperature of 100° C. or less, and $R_5$ represents a hydrocarbon radical containing at least two carbons, n has a value of 1 to 3 and x has a value of 1 to 3, but cannot be greater than n.

2. The polyaspartate ester of claim 1 wherein $R_1$ and $R_2$ represent a methyl, ethyl or butyl group, $R_3$ and $R_4$ represent hydrogen and x is 1.

3. The polyaspartate ester of claim 1 wherein n is 1.

4. The polyaspartate ester of claim 2 wherein n is 1.

5. A process for the preparation of hyperbranched polyaspartate esters which comprises self condensing, via a transesterification reaction, at least a portion of the hydroxy and ester groups of a hydroxy aspartate corresponding to the formula

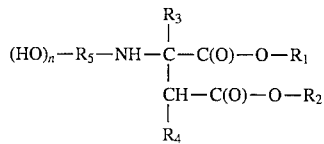 (II)

wherein $R_1$ and $R_2$ may be identical or different and represent organic groups which are inert towards isocyanate groups at a temperature of 100° C. or less, $R_3$ and $R_4$ may be identical or different and represent hydrogen or organic groups which are inert towards isocyanate groups at a temperature of 100° C. or less, and $R_5$ represents a hydrocarbon radical containing at least two carbons and n has a value of 1 to 3, at a temperature of 60° to 240° C. to form hyperbranched polyaspartate esters and eliminating alcohols having the formula $R_1$—OH and/or $R_2$—OH.

6. The process of claim 5 wherein $R_1$ and $R_2$ represent a methyl, ethyl or butyl group, $R_3$ and $R_4$ represent hydrogen and x is 1.

7. The process of claim 5 wherein n is 1.

8. The process of claim 6 wherein n is 1.

9. The process of claim 5 wherein said hydroxy aspartate is mixed with a positive amount of up to 80% by weight, based on the total weight of the monomers, of a non-amine containing hydroxy acid.

* * * * *